(12) United States Patent
Jaeger et al.

(10) Patent No.: US 9,055,948 B2
(45) Date of Patent: Jun. 16, 2015

(54) VASO-OCCLUSIVE DEVICES COMPRISING COMPLEX-SHAPE PROXIMAL PORTION AND SMALLER DIAMETER DISTAL PORTION

(75) Inventors: Kevin M. Jaeger, Pleasanton, CA (US); Clifford Teoh, Los Altos, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 1654 days.

(21) Appl. No.: 11/270,035

(22) Filed: Nov. 9, 2005

(65) Prior Publication Data

US 2006/0100661 A1   May 11, 2006

Related U.S. Application Data

(60) Provisional application No. 60/626,706, filed on Nov. 9, 2004.

(51) Int. Cl.
   *A61M 29/00* (2006.01)
   *A61B 17/12* (2006.01)
   *A61L 31/02* (2006.01)

(52) U.S. Cl.
   CPC ..... *A61B 17/12022* (2013.01); *A61B 17/12113* (2013.01); *A61B 17/12145* (2013.01); *A61B 17/1215* (2013.01); *A61B 2017/12063* (2013.01); *A61L 31/022* (2013.01); *A61B 2017/12054* (2013.01)

(58) Field of Classification Search
   CPC .................. A61B 17/12022; A61B 17/12113; A61B 17/12145; A61B 17/1215
   USPC .............. 606/1, 32, 191, 213, 200, 194, 108, 606/157, 195; 604/265, 523, 525, 529; 128/897
   See application file for complete search history.

(56) References Cited

U.S. PATENT DOCUMENTS

| | | |
|---|---|---|
| 3,174,851 A | 3/1965 | Buehler |
| 3,351,463 A | 11/1967 | Rozner |
| 3,753,700 A | 8/1973 | Harrison et al. |
| 4,739,768 A | 4/1988 | Engelson |
| 4,994,069 A | 2/1991 | Ritchart et al. |
| 5,226,911 A | 7/1993 | Chee et al. |
| 5,234,437 A | 8/1993 | Sepetka |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,334,210 A | 8/1994 | Gianturco |
| 5,350,397 A | 9/1994 | Palermo et al. |

(Continued)

FOREIGN PATENT DOCUMENTS

| | | |
|---|---|---|
| WO | WO 02/45596 A2 | 6/2002 |
| WO | WO 02/051460 A2 | 7/2002 |

*Primary Examiner* — Thomas McEvoy
*Assistant Examiner* — Julie A Szpira
(74) *Attorney, Agent, or Firm* — Vista IP Law Group LLP

(57) ABSTRACT

This is a device for occluding a space within the body. In particular, the device comprises a proximal portion having a complex, three-dimensional shape and a distal portion, where the diameter of the shape defined by the distal portion is smaller than the diameter of the shape defined by the proximal portion. The devices may be placed in a desired site within a mammal and are useful in occluding devices.

13 Claims, 1 Drawing Sheet

(56) References Cited

U.S. PATENT DOCUMENTS

| | | | |
|---|---|---|---|
| 5,354,295 A | 10/1994 | Guglielmi et al. | |
| 5,382,259 A | 1/1995 | Phelps et al. | |
| 5,423,829 A | 6/1995 | Pham et al. | |
| 5,522,822 A | 6/1996 | Phelps et al. | |
| 5,522,836 A | 6/1996 | Palermo | |
| 5,536,274 A | 7/1996 | Neuss | |
| 5,537,338 A | 7/1996 | Coelho | |
| 5,624,461 A | 4/1997 | Mariant | |
| 5,639,277 A | 6/1997 | Mariant et al. | |
| 5,649,949 A | 7/1997 | Wallace et al. | |
| 5,690,666 A | 11/1997 | Berenstein et al. | |
| 5,826,587 A | 10/1998 | Berenstein et al. | |
| 5,911,731 A | 6/1999 | Pham et al. | |
| 5,935,145 A | 8/1999 | Villar et al. | |
| 5,964,797 A | 10/1999 | Ho | |
| 6,024,765 A | 2/2000 | Wallace et al. | |
| 6,136,015 A | 10/2000 | Kurz et al. | |
| 6,156,061 A | 12/2000 | Wallace et al. | |
| 6,171,326 B1 | 1/2001 | Ferrera et al. | |
| 6,299,627 B1 | 10/2001 | Eder et al. | |
| 6,533,801 B2 | 3/2003 | Wallace et al. | |
| 6,585,754 B2 | 7/2003 | Wallace et al. | |
| 6,623,493 B2 | 9/2003 | Wallace et al. | |
| 6,635,069 B1 | 10/2003 | Teoh et al. | |
| 6,638,291 B1 * | 10/2003 | Ferrera et al. | 606/191 |
| 6,860,893 B2 | 3/2005 | Wallace et al. | |
| 2001/0034531 A1 | 10/2001 | Ho et al. | |
| 2002/0002382 A1 * | 1/2002 | Wallace et al. | 606/191 |
| 2002/0019647 A1 | 2/2002 | Wallace et al. | |
| 2002/0107534 A1 * | 8/2002 | Schaefer et al. | 606/151 |
| 2002/0151926 A1 * | 10/2002 | Wallace et al. | 606/200 |
| 2003/0120302 A1 | 6/2003 | Minck, Jr. et al. | |
| 2005/0149109 A1 | 7/2005 | Wallace et al. | |
| 2005/0192618 A1 * | 9/2005 | Porter | 606/200 |

* cited by examiner

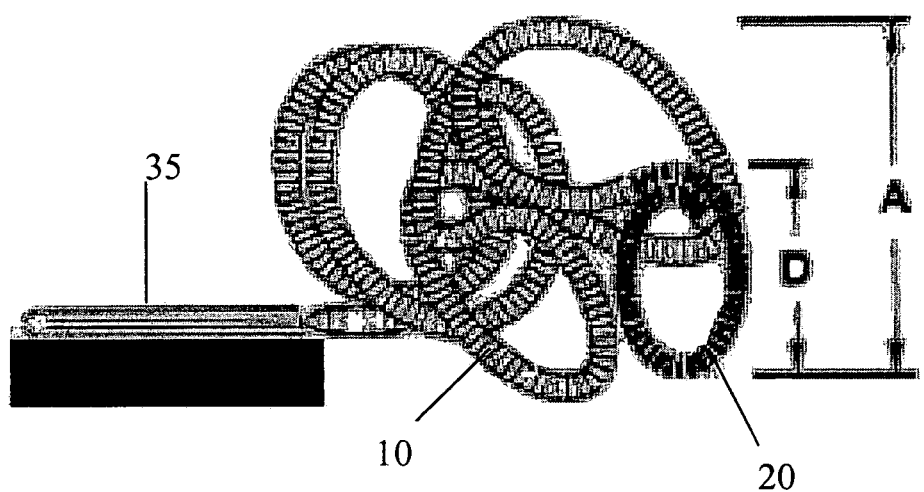

VASO-OCCLUSIVE DEVICES COMPRISING COMPLEX-SHAPE PROXIMAL PORTION AND SMALLER DIAMETER DISTAL PORTION

CROSS-REFERENCE TO RELATED APPLICATIONS

This application claims the benefit of U.S. provisional patent application No. 60/626,706 (filed Nov. 9, 2004) the disclosure of which is incorporated by reference in its entirety for all purposes.

FIELD OF THE INVENTION

Compositions and methods for repair of aneurysms are described. In particular, vaso-occlusive devices are disclosed, as are methods of making and using these devices.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. Vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings that may be dimensioned to engage the walls of the vessels. Other less stiff helically coiled devices have been described, as well as those involving woven braids. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of "complex" three-dimensional shapes. The secondary shapes of the disclosed coils include "flower" shapes and double vortices. A random shape is described, as well. Other less stiff helically coiled devices have been described, as well as those involving woven braids. See, e.g., U.S. Pat. No. 6,299,627.

Other three-dimensional vaso-occlusive devices have been described. U.S. Pat. No. 5,624,461 to Mariant describes a three-dimensional in-filling vaso-occlusive coil. U.S. Pat. No. 5,639,277 to Mariant et al. describes embolic oils having twisted helical shapes and U.S. Pat. No. 5,649,949 to Wallace et al. describes variable cross-section conical vaso-occlusive coils.

U.S. Pat. No. 5,334,210 to Gianturco, describes a vascular occlusion assembly comprising a foldable material occlusion bag and a filled member, for example, a helical coil with a J-hook on the proximal end. The bag expands to form a diamond shape structure and the filler member inside the bag is forced into a convoluted configuration as it is advanced into the cavity of the foldable bag.

Implantable devices using variously shaped coils are shown in U.S. Pat. No. 5,537,338 to Purdy. Purdy described a multi-element intravascular occlusion device in which shaped coils may be employed. U.S. Pat. No. 5,536,274 to Neuss shows a spiral implant that may assume a variety of secondary shapes. Some complex shapes can be formed by interconnecting two or more of the spiral-shaped implants.

Vaso-occlusive coils having little or no inherent secondary shape have also been described. For instance, co-owned U.S. Pat. Nos. 5,690,666 and 5,826,587 by Berenstein et al., describes coils having little or no shape after introduction into the vascular space.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

However, none of the above documents show a device as described herein.

SUMMARY OF THE INVENTION

Thus, this invention includes novel occlusive compositions as well as methods of using and making these compositions.

Described herein are vaso-occlusive devices comprising (i) a proximal portion having a complex, three-dimensional relaxed configuration and a first overall diameter in the relaxed configuration and (ii) a distal portion having a diameter less than the diameter of the proximal portion. The distal portion may be a two-dimensional or three-dimensional configuration, for example, one or more loops.

In any of the devices described herein, the diameter of the distal portion is at least 10% smaller than the diameter of the proximal portion, more preferably at least 25% smaller than the diameter of the proximal portion, even more preferably at least 50% smaller than the diameter of the proximal portion, and even more preferably at least 75% smaller than the diameter of the proximal portion.

Any of the devices described herein may further comprise a severable junction detachably which may be connected to a delivery device (e.g., pusher element). The detachment junction can be positioned anywhere on the device, for example at one or both ends of the device. In certain embodiments, the severable junction(s) are, an electrolytically detachable assembly adapted to detach by imposition of a current; a mechanically detachable assembly adapted to detach by movement or pressure; a thermally detachable assembly adapted to detach by localized delivery of heat to the junction; a radiation detachable assembly adapted to detach by delivery of electromagnetic radiation to the junction or combinations thereof.

In another aspect, a method of occluding a body cavity is described, the method comprising introducing a vaso-occlusive device as described herein into the body cavity. In certain embodiments, the body cavity is an aneurysm.

In another aspect, the invention includes a method of occluding a body cavity comprising introducing any of the vaso-occlusive devices described herein into a body cavity (e.g., an aneurysm).

These and other embodiments of the subject invention will readily occur to those of skill in the art in light of the disclosure herein.

BRIEF DESCRIPTION OF THE FIGURES

FIG. 1 is an overview depicting an exemplary device as described herein. Proximal portion (10) has an overall diameter ("A") that is substantially larger than the diameter ("D") of distal portion (20).

It is to be understood that the drawing depicts an exemplary embodiment and is not to be considered limiting in scope.

DESCRIPTION OF THE INVENTION

Occlusive (e.g., embolic) compositions are described. The compositions described herein find use in vascular and neurovascular indications and are particularly useful in treating aneurysms, for example small-diameter, curved or otherwise difficult to access vasculature, for example aneurysms, such as cerebral aneurysms. Methods of making and using these vaso-occlusive elements also form aspects of this invention.

All documents (publications, patents and patent applications) cited herein, whether above or below, are hereby incorporated by reference in their entireties.

It must be noted that, as used in this specification and the appended claims, the singular forms "a", "an", and "the" include plural referents unless the content clearly dictates otherwise. Thus, for example, reference to a device comprising "a loop" includes devices comprising of two or more loops.

The self-forming coil designs of the present invention are particularly useful in treating aneurysms. The designs described herein provide an improvement over known devices, for example in terms of ease of deployment. The inclusion of a distal portion having a diameter that is smaller than the diameter of the main proximal portion of the device allows the devices to be placed into the target vessel more easily. In particular, embolic coils have a tendency for the initial (distal) loop being introduced into an aneurysm to herniate into the parent vessel as the first (distal) loop is inserted. The designs described herein increase the ease of introducing a complex-shaped coil into an aneurysm or other lesion by making the distal loop substantially smaller than the more proximal loops and thus smaller than the dimensions of the aneurysm, so that it will "sit" in the aneurysmal space without "snaking" out before the remaining loops are deployed.

Thus, the devices described herein comprise a proximal portion having a three-dimensional shape defining a first diameter and a second distal portion having a shape defining a second diameter, where the second diameter is substantially smaller than first diameter.

The three-dimensional shape of the distal and proximal portions may be the same or different. For example, in certain embodiments, both the proximal and distal portions have complex three-dimensional shapes. By "complex" is meant any three-dimensional shape that defines multiple planes. Non-limiting examples of complex, three-dimensional shapes include spherical, elliptical, cube-like, random, flower-shaped, vortex-shaped, conical, spherical, non-overlapping loop structure, etc. See, e.g., U.S. Pat. Nos. 4,994,069; 5,624,461; 5,649,949; 5,522,822; 5,935,145; 5,690,666; 5,826,587; and 6,635,069. Similarly, the distal portion can assume a variety of these configurations.

Alternatively, in certain preferred embodiments, the proximal portion has a complex three-dimensional shape while the distal portion has a two-dimensional shape (such as a loop or J-shape). A "two-dimensional" shape refers to any shape that where the configuration of that portion of the devices defines a plane. It will be apparent that in order to have a diameter (e.g., a diameter that is smaller than that of the overall diameter of the proximal portion), a two-dimensional distal portion must include some kind of circular shape, for example, a loop, a J-shape, an ellipse, etc. In a preferred embodiment, the distal portion is a single loop configuration.

FIG. 1 shows an exemplary device comprising a complex embolic coil of any non-helical complex shape (10), with the distal-most loop or loops (20) shown in darker gray. The distal most component (20) has a diameter ("D") substantially smaller than the overall diameter ("A") of the loops in the complex-shaped portion (10) of the device. Also shown in FIG. 1 is deployment catheter (35).

In one preferred embodiment, the diameter of the distal portion (20) is approximately 75% of the overall diameter (e.g., the diameter of one or more of the loops) in the complex portion. However, it will be apparent that the diameter of the distal portion (e.g., loop) ("D") may be more or less than 75% of the diameter of the proximal, complex portion ("A"), so long as the diameter of the distal portion is smaller than the diameter of the proximal portion.

As shown in FIG. 1, the two portions are preferably made out of the same materials and are also preferably integral to each other. However, it is also contemplated that the two portions can be made of different materials and/or that they can be made separately and joined after manufacture.

The material(s) used in constructing the vaso-occlusive devices described herein may be any of a wide variety of materials; preferably, the material is a radio-opaque material such as a metal or a polymer. Suitable metals and alloys include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The device may also be of any of a wide variety of stainless steels if some sacrifice of radiopacity may be tolerated. Very desirable materials of construction, from a mechanical point of view, are materials that maintain their shape despite being subjected to high stress. Certain "super-elastic alloys"

include nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys that will tolerate significant flexing without deformation even when used as a very small diameter wire. If a superelastic alloy such as nitinol is used in the device, the diameter of the coil wire may be significantly smaller than that used when the relatively more ductile platinum or platinum/tungsten alloy is used as the material of construction.

The devices may also comprise a wide variety of synthetic and natural polymers, such as Dacron (polyester), polyglycolic acid, polylactic acid, fluoropolymers (polytetrafluoroethylene), Nylon (polyamide), or even silk. Other exemplary polymers that may be used include, but are not limited to, polyurethanes (including copolymers with soft segments containing esters, ethers and carbonates), ethers, acrylates (including cyanoacrylates), olefins (including polymers and copolymers of ethylene, propylene, butenes, butadiene, styrene, and thermoplastic olefin elastomers), polydimethyl siloxane-based polymers, polyethyleneterephthalate, cross-linked polymers, non-cross linked polymers, rayon, cellulose, cellulose derivatives such nitrocellulose, natural rubbers, polyesters such as lactides, glycolides, caprolactones and their copolymers and acid derivatives, hydroxybutyrate and polyhydroxyvalerate and their copolymers, polyether esters such as polydioxinone, anhydrides such as polymers and copolymers of sebacic acid, hexadecandioic acid and other diacids, orthoesters may be used. Should a polymer be used as the major component of the vaso-occlusive member, it is desirably filled with some amount of a known radiopaque material such as powdered tantalum, powdered tungsten, bismuth oxide, barium sulfate, and the like.

The overall diameter of the device as deployed is generally between 2 and 30 millimeters (or any diameter therebetween), for example 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm. Most aneurysms within the cranial vasculature can be treated by one or more devices having those diameters. Of course, such diameters are not a critical aspect of the invention.

Also contemplated in this invention is the attachment of various fibrous materials to the inventive coil for the purpose of adding thrombogenicity to the resulting assembly. The fibrous materials may be attached in a variety of ways. A series of looping fibers may be looped through or tied to coil and continue axially down the coil. Another variation is by tying the tuft to the coil. Tufts may be tied at multiple sites through the coil to provide a vast area of embolus forming sites. The primary coil may be covered by a fibrous braid. The method for producing the former variation is described in U.S. Pat. Nos. 5,226,911 and 5,304,194 to Chee. The method of producing the fibrous braid is described in U.S. Pat. No. 5,382,259, issued Jan. 17, 1995, to Phelps and Van.

The coils described herein can also include additional additives, for example, any material that exhibits biological activity in vivo, such as co-solvents, plasticizers, coalescing solvents, bioactive agents, antimicrobial agents, antithrombogenic agents (e.g., heparin), antibiotics, pigments, radiopacifiers and/or ion conductors which may be coated using any suitable method or may be incorporated into the element(s) during production. See, e.g., co-owned U.S. patent application Ser. No. 10/745,911, U.S. Pat. No. 6,585, 754 and WO 02/051460, incorporated by reference in their entireties herein. Thus, bioactive materials can be coated onto the device (e.g., heparin) and/or can be placed in the vessel prior to, concurrently or after placement of one or more devices as described herein.

One of more of the elements may also be secured to each other at one or more locations. For example, to the extent that various elements are thermoplastic, they may be melted or fused to other elements of the devices. Alternatively, they may be glued or otherwise fastened. Furthermore, the various elements may be secured to each other in one or more locations.

Methods of Use

The devices described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place vaso-occlusive device at the target site but yet with a sufficient portion of the distal end of the delivery mechanism protruding from the distal end of the catheter to enable detachment of the implantable vaso-occlusive device. For use in peripheral or neural surgeries, the delivery mechanism will normally be about 100-200 cm in length, more normally 130-180 cm in length. The diameter of the delivery mechanism is usually in the range of 0.25 to about 0.90 mm. Briefly, occlusive devices (and/or additional components) described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g. vaso-occlusive members and/or liquid embolics and bioactive materials) which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the vaso-occlusive device at the distal end, is advanced through the catheter.

Once the selected site has been reached, the vaso-occlusive device is extruded, for example by loading onto a pusher wire. Preferably, the vaso-occlusive device is loaded onto the pusher wire via a mechanically or electrolytically cleavable junction (e.g., a GDC-type junction that can be severed by application of heat, electrolysis, electrodynamic activation, coherent laser light or other means). Additionally, the vaso-occlusive device can be designed to include multiple detachment points, as described in co-owned U.S. Pat. Nos. 6,623,493 and 6,533,801 and International Patent publication WO 02/45596. They are held in place by gravity, shape, size, volume, magnetic field or combinations thereof.

Modifications of the procedure and vaso-occlusive devices described above, and the methods of using them in keeping with this invention will be apparent to those having skill in this mechanical and surgical art.

What is claimed is:

1. A vaso-occlusive device having an overall diameter in a relaxed configuration, the device comprising
   (i) a proximal portion having a random, complex, three-dimensional relaxed configuration and a first overall diameter that defines the overall diameter of the device in the relaxed configuration and
   (ii) a distal portion having a circular two-dimensional or a three-dimensional shape and a second overall diameter in the relaxed configuration, wherein the second overall diameter is less than the first overall diameter, and wherein said distal portion does not extend distally beyond said proximal portion in the relaxed configuration.

2. The device of claim 1, wherein the distal portion comprises a two-dimensional configuration.

3. The device of claim 2, wherein the distal portion comprises a loop.

4. The device of claim 2, wherein the distal portion comprises a J-shape.

5. The device of 1, wherein the second overall diameter is at least 10% smaller than the first overall diameter.

6. The device of claim 5, wherein the second overall diameter is at least 25% smaller than the first overall diameter.

7. The device of claim 5, wherein the second overall diameter is at least 50% smaller than the first overall diameter.

8. The device of claim 5, wherein the second overall diameter is at least 75% smaller than the first overall diameter of the proximal portion.

9. The device of claim 1, further comprising a severable junction.

10. The device of claim 9, wherein the severable junction is detachably connected to a delivery mechanism.

11. The device of claim 9, wherein the severable junction is selected from the group consisting of an electrolytically detachable junction adapted to detach by imposition of a current, a mechanically detachable junction adapted to detach by movement or pressure, a thermally detachable junction adapted to detach by localized delivery of heat to the junction, a radiation detachable junction adapted to detach by delivery of electromagnetic radiation to the junction and combinations thereof.

12. A method of occluding a body cavity comprising the step of introducing a vaso-occlusive device according to claim 1 into the body cavity.

13. The method of claim 12, wherein the body cavity is an aneurysm.

* * * * *